US012778768B2

(12) United States Patent
Gantick et al.

(10) Patent No.: US 12,778,768 B2
(45) Date of Patent: Nov. 3, 2026

(54) SPINAL INTERBODY IMPLANTS

(71) Applicant: K2M, Inc., Leesburg, VA (US)

(72) Inventors: Jason Noel Gantick, Purcellville, VA (US); Ailon Haileyesus, Centreville, VA (US); Joseph Michael Meyer, Bethel, OH (US); Eleftherios Louvis, Carrigaline (IE); Leonid Pavlovsky, Parsippany, NJ (US); Joseph Henry Robinson, New City, NY (US); Steven Willis, Midland Park, NJ (US)

(73) Assignee: VB Spine LLC, Sterling, VA (US)

( * ) Notice: Subject to any disclaimer, the term of this patent is extended or adjusted under 35 U.S.C. 154(b) by 259 days.

(21) Appl. No.: 18/029,265

(22) PCT Filed: Oct. 1, 2021

(86) PCT No.: PCT/US2021/053153
§ 371 (c)(1),
(2) Date: Mar. 29, 2023

(87) PCT Pub. No.: WO2022/072816
PCT Pub. Date: Apr. 7, 2022

(65) Prior Publication Data

US 2023/0404773 A1 Dec. 21, 2023

Related U.S. Application Data

(60) Provisional application No. 63/086,897, filed on Oct. 2, 2020.

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2002/30011* (2013.01);
(Continued)

(58) Field of Classification Search
CPC ........ A61F 2/447; A61F 2/44; A61F 2/30771; A61F 2002/30011; A61F 2002/30784; A61F 2002/3092; A61F 2002/30971
(Continued)

(56) References Cited

U.S. PATENT DOCUMENTS

| | | | |
|---|---|---|---|
| 4,863,538 A | 9/1989 | Deckard | |
| 4,944,817 A | 7/1990 | Bourell et al. | |

(Continued)

FOREIGN PATENT DOCUMENTS

| | | |
|---|---|---|
| EP | 1537839 A1 | 6/2005 |
| WO | 2017106780 A1 | 6/2017 |

(Continued)

OTHER PUBLICATIONS

International Search Report for Appln. No. PCT/US2021/054765 mailed Feb. 14, 2022 (4 pages).

(Continued)

*Primary Examiner* — Jessica Weiss
(74) *Attorney, Agent, or Firm* — Lerner David LLP

(57) ABSTRACT

Disclosed herein are embodiments of a spinal implant having structures that incorporate a solid material and a porous material. The solid material provides the implant with an outer shell for structural integrity while the porous material, distributed within an interior of the implant as a lattice structure for example, promotes visibility of the implant in radiological imaging, promotes bony ingrowth and cell attachment and improves wicking.

12 Claims, 8 Drawing Sheets

(52) U.S. Cl.
CPC ............... *A61F 2002/30784* (2013.01); *A61F 2002/3092* (2013.01); *A61F 2002/3093* (2013.01); *A61F 2002/30971* (2013.01)

(58) Field of Classification Search
USPC ........................................... 623/17.11–17.16
See application file for complete search history.

(56) References Cited

U.S. PATENT DOCUMENTS

| | | | | |
|---|---|---|---|---|
| 5,017,753 | A | 5/1991 | Deckard | |
| 5,076,869 | A | 12/1991 | Bourell et al. | |
| 5,607,424 | A * | 3/1997 | Tropiano | A61F 2/4455 606/17 |
| 5,609,635 | A | 3/1997 | Michelson | |
| 6,039,762 | A * | 3/2000 | Mckay | A61L 27/04 606/247 |
| 6,136,031 | A | 10/2000 | Middleton | |
| 6,494,883 | B1 * | 12/2002 | Ferree | A61F 2/28 606/247 |
| 7,537,664 | B2 | 5/2009 | O'Neill et al. | |
| 9,987,051 | B2 | 6/2018 | Nunley et al. | |
| D824,518 | S | 7/2018 | Wilson et al. | |
| 10,028,841 | B2 | 7/2018 | Moore et al. | |
| 10,213,317 | B2 * | 2/2019 | Bishop | A61F 2/447 |
| 10,420,597 | B2 * | 9/2019 | Papangelou | A61B 17/0401 |
| 10,512,545 | B2 | 12/2019 | Arnone | |
| 10,772,732 | B1 * | 9/2020 | Miller | A61F 2/3094 |
| 10,835,388 | B2 * | 11/2020 | Milz | A61F 2/4455 |
| 11,826,265 | B2 | 11/2023 | McLean et al. | |
| 2002/0161443 | A1 | 10/2002 | Michelson | |
| 2003/0208274 | A1 * | 11/2003 | Davis | A61F 2/442 623/17.16 |
| 2006/0052872 | A1 * | 3/2006 | Studer | A61F 2/4425 623/17.13 |
| 2006/0129242 | A1 | 6/2006 | Bergeron et al. | |
| 2007/0179610 | A1 | 8/2007 | Biedermann et al. | |
| 2007/0260324 | A1 * | 11/2007 | Joshi | A61F 2/4465 623/17.11 |
| 2008/0077244 | A1 * | 3/2008 | Robinson | A61F 2/442 623/17.15 |
| 2008/0154379 | A1 | 6/2008 | Steiner et al. | |
| 2008/0161927 | A1 | 7/2008 | Savage et al. | |
| 2010/0222750 | A1 * | 9/2010 | Cheng | A61F 2/442 606/246 |
| 2011/0040384 | A1 | 2/2011 | Junn et al. | |
| 2012/0191188 | A1 | 7/2012 | Huang | |
| 2012/0316650 | A1 | 12/2012 | Ullrich, Jr. et al. | |
| 2012/0330420 | A1 * | 12/2012 | Brodke | A61L 27/32 623/17.16 |
| 2013/0096685 | A1 | 4/2013 | Ciupik et al. | |
| 2013/0166793 | A1 | 6/2013 | Shahar et al. | |
| 2013/0304211 | A1 | 11/2013 | Trautwein et al. | |
| 2014/0107786 | A1 | 4/2014 | Geisler et al. | |
| 2016/0038301 | A1 * | 2/2016 | Wickham | A61F 2/4455 623/17.16 |
| 2016/0128843 | A1 * | 5/2016 | Tsau | A61L 27/34 428/164 |
| 2016/0213405 | A1 | 7/2016 | Moore et al. | |
| 2016/0213487 | A1 | 7/2016 | Wilson et al. | |
| 2016/0377113 | A1 | 12/2016 | Jimenez et al. | |
| 2017/0333205 | A1 | 11/2017 | Joly et al. | |
| 2017/0354513 | A1 * | 12/2017 | Maglaras | A61F 2/4455 |
| 2018/0110624 | A1 | 4/2018 | Arnone | |
| 2018/0256336 | A1 | 9/2018 | Mueller et al. | |
| 2018/0263785 | A1 | 9/2018 | Vishnubhotla et al. | |
| 2018/0296363 | A1 | 10/2018 | Berry | |
| 2018/0325692 | A1 | 11/2018 | Moore et al. | |
| 2019/0008562 | A1 | 1/2019 | Melton et al. | |
| 2019/0076258 | A1 | 3/2019 | Black et al. | |
| 2019/0076266 | A1 | 3/2019 | Trudeau et al. | |
| 2019/0083282 | A1 | 3/2019 | Roeder et al. | |
| 2019/0183653 | A1 * | 6/2019 | Gregersen | A61F 2/447 |
| 2019/0343644 | A1 | 11/2019 | Ryan et al. | |
| 2019/0343645 | A1 * | 11/2019 | Miccio | A61F 2/30771 |
| 2019/0343652 | A1 | 11/2019 | Petersheim et al. | |
| 2020/0038198 | A1 | 2/2020 | Miccio | |
| 2020/0046512 | A1 * | 2/2020 | Newman | A61F 2/4455 |
| 2020/0093612 | A1 | 3/2020 | Blain et al. | |
| 2020/0268523 | A1 | 8/2020 | Barthold et al. | |
| 2020/0289714 | A1 * | 9/2020 | Snell | A61F 2/30771 |
| 2021/0038403 | A1 | 2/2021 | Neary | |
| 2021/0077267 | A1 | 3/2021 | Morrison et al. | |
| 2021/0106433 | A1 | 4/2021 | Motley et al. | |
| 2021/0244548 | A1 | 8/2021 | Ahn | |
| 2022/0160519 | A1 | 5/2022 | Northcutt et al. | |
| 2022/0296386 | A1 | 9/2022 | Fang et al. | |
| 2023/0321324 | A1 | 10/2023 | Reith et al. | |
| 2023/0404773 | A1 | 12/2023 | Gantick et al. | |

FOREIGN PATENT DOCUMENTS

| | | | |
|---|---|---|---|
| WO | 2019165445 | A1 | 8/2019 |
| WO | 2019191149 | A1 | 10/2019 |

OTHER PUBLICATIONS

Partial International Search Report and Associated Communication issued in Appln. No. PCT/US2021/053153 dated Mar. 17, 2022 (13 pages).
International Search Report and Written Opinion issued in Appln. No. PCT/US2021/053153 mailed May 11, 2022 (20 pages).
Extended European Search Report issued in Appln. No. 25202533.3 dated Dec. 4, 2025 (14 pages).

* cited by examiner

SPINAL INTERBODY IMPLANTS

CROSS-REFERENCE TO RELATED APPLICATIONS

The present application is a national phase entry under 35 U.S.C. § 371 of International Application No. PCT/US2021/053153, filed on Oct. 1, 2021, which claims the benefit of the filing date of U.S. Provisional Application No. 63/086,897 filed on Oct. 2, 2020, the disclosure of which is hereby incorporated by reference herein in its entirety.

BACKGROUND OF THE INVENTION

Back pain can be caused by many different maladies, some of which originate in the intervertebral discs of the spine. Typical problems with intervertebral discs include, among others, degeneration, bulging, herniation, thinning and abnormal movement. One widely used method of treatment for such disc problems is a spinal fusion procedure, whereby an affected disc is removed and the adjacent vertebral bodies are fused together through the use of interbody spacers, implants or the like.

The aforementioned implants often rely upon fixation elements to ensure engagement between the devices and the bone of the existing vertebral bodies. This coupled with the normal compressive load of the spine acts to keep the implant in place until bone can grow from the existing vertebral bodies into and through the implant. To encourage bone growth, the implants are often pre-loaded with bone growth promoting material and thereafter placed into the spine. Bone growth promoting material may include naturally occurring bone, artificial materials or the like.

To further ensure a strong implant-bone connection, some existing implants include porous material that promotes bone ingrowth. Although there is little doubt that bone ingrowth is beneficial in maintaining an implant in place, these implants are often very difficult and expensive to manufacture. Additionally, existing implants that include porous material often include such material in a limited manner Often times, because of manufacturing or strength concerns or the like, the porous material is limited to a thin layer covering the upper and lower surfaces of the implant, which only allows for a small amount of bone to grow into the implant. Moreover, implants that utilize material that itself has a lower modulus of elasticity may suffer from reduced load bearing capacity.

Therefore, there exists a need for an improved spinal implant that provides improved bone ingrowth capacity while also having suitable load bearing capacity for use in spinal applications.

BRIEF SUMMARY OF THE INVENTION

The present disclosure relates to spinal implants and methods associated with the same. In particular, the application relates to spinal implants made from a combination of porous and solid materials and the methods for fabricating such implants.

In one aspect, the present disclosure involves spinal interbody implants that may include both solid and porous parts. Several embodiments are illustrated having various structures and configurations for optimizing the advantages of including both solid and porous regions in a body of an implant. Certain embodiments exploit the unique advantages of solid and porous materials having an outer structure made of a solid material and an inner structure or inner region defined by the outer structure that is more porous. Other embodiments may include alternating regions of solid and porous materials. Such configurations include solid material for characteristics such as, e.g., improved load-bearing and porous material for, e.g., promoting bone in-growth, cell attachment and visibility in fluoroscopic imaging, among other things.

In certain embodiments, the present disclosure relates to a spinal interbody implant. In a first example, a spinal interbody implant may have a body including a peripheral layer at least partially enclosing the body. The implant may have an inner region within the peripheral layer defined by a plurality of interconnected tubes. At least one tube of the interconnected tubes may include an outer tubular part and an inner fill part disposed within a hollow interior of the outer tubular part. The outer tubular part may be a first material with a first porosity and the inner fill part may be a second material with a second porosity greater than the first porosity. In a second example, the implant of the first example may have the first material and the second material be the same. In a third example, the first material of the first example may be titanium and the second material may be a titanium alloy. In a fourth example, the second porosity of any one of the first through third examples may be in a range from 55-65% of a volume of the inner fill part. In a fifth example, at least one of the plurality of tubes of any one of the first through fourth examples may have a first end on a first surface of the peripheral layer and a second end on a second surface of the peripheral layer. In a sixth example, at least one of the plurality of tubes of any one of the first through fifth examples may extend through one of the first and second surfaces of the peripheral layer. In a seventh example, the plurality of tubes of any one of the first through sixth examples may extend in parallel in the first direction, the plurality of tubes being disposed evenly throughout the inner region. In an eighth example, the plurality of tubes of any one of the first through seventh examples may define a lattice structure within the inner region. In a ninth example, the peripheral layer may of any one of the first through eighth examples may include an upper plate and a lower plate such that the plurality of interconnected tubes extend therebetween. In a tenth example, the peripheral layer of any one of the ninth example may include a plurality of struts extending between the upper plate and the lower plate, the plurality of struts being oriented at an angle relative to each of the plurality of interconnected tubes. In an eleventh example, the plurality of tubes of any one of the first through tenth examples may include a first group of tubes and a second group of tubes, the first group of tubes being approximately in parallel with one another and oriented in a first direction, and the second group of tubes being approximately in parallel with one another and oriented in a second direction different from the first direction, the plurality of tubes defining a lattice structure within the inner region. In a twelfth example, the plurality of interconnected tubes of any one of the first through eleventh examples may include two or more interconnected tubes in a first layer and two or more interconnected tubes in a second layer parallel and adjacent to the first layer. In a thirteenth example, the outer tubular part of the at least one tube of the plurality of tubes of any one of the first through twelfth examples may include a series of openings therethrough. In a fourteenth example, the series of openings through the outer tubular part of the at least one tube of the thirteenth example may be filled with the second material. In a fifteenth example the first material of any one of the first through fourteenth examples may be titanium. In a sixteenth example, the second material of any one of the first through fifteenth examples may be titanium.

In another first example, a spinal interbody implant may have a body sized for placement in an intervertebral disc space. The body may include a primary outer structure and a plurality of inner structures disposed within channels of the primary outer structure, each of the plurality of inner structures including an outer shell and an inner fill with a different porosity than the outer shell. The primary outer structure may have a first porosity and the inner fill of each of the plurality of inner structures may have a second porosity greater than the first porosity. The plurality of inner structures may have a shape matching a shape of a respective channel, the plurality of inner structures extending between opposite outer surfaces of the primary outer structure. In a second example, each of the plurality of inner structures of the first example may fill a volume of a respective channel in the primary outer structure such that a total volume of the body is filled by a combination of the primary outer structure and the plurality of inner structures. In a third example, the outer part of each of the plurality of inner structures of any one of the first or second examples may include a plurality of openings distinguishable from the porosity of the outer shell such that the inner fill of the plurality of inner structures directly contacts a surface of the primary outer structure. In a fourth example, the channels in the primary outer structure of any one of the first through third examples may each be defined by a wall, and the way may be at least partially porous so that a line of contact between the primary outer structure and the plurality of inner structures is in part non-circular around each inner structure along a length of each inner structure. In a fifth example, the implant of any one of the first through fourth examples may include at least one second inner structure having an outer shell with a hollow interior no more than partially filled by an inner fill material. In a sixth example, the plurality of inner structures of any one of the first through fifth examples may be spread evenly throughout the primary outer structure. In a seventh example, a combination of the primary outer structure and the plurality of inner structures of any one of the first through sixth examples may occupy a volume less than a full volume of the body. In an eighth example, the plurality of inner structures of any one of the first through seventh examples may form an interconnected network of inner structures within the outer primary structure, the inner structures may be evenly distributed within the volume of the primary structure.

In a further first example, a spinal interbody implant may have a plurality of layers, each layer being a patterned lattice structure and interconnected with at least one other layer of the plurality of layers. The plurality of layers may each have a first layer that has a structure including a first plurality of struts oriented in a first direction and a second plurality of struts oriented in a second direction. At least one strut of the first plurality of struts may cross at least one strut of the second plurality of struts such that the struts are interconnected. A first strut of the first plurality of struts may have a length and a first porosity at a first crossing with a second strut of the second plurality of struts and a second porosity at a second crossing with a third strut of the second plurality of struts. The second strut may be adjacent to the third strut. The first porosity may be different from the second porosity. In a second example, the material at one of the first crossing and the second crossing of the first example may have a porosity in a range from 55-60% of volume. In a third example, the first plurality of struts and the second plurality of struts of the first or second examples may each be linear throughout their length. In a fourth example, the structure of any one of the first through third examples may have a first pattern throughout its surface area. In a fifth example, the plurality of layers of any one of the first through fourth examples may include a second layer adjacent and attached to the first layer, a second structure of the second layer having the first pattern throughout its surface area. In a sixth example, the second structure of the second layer of any one of the first through fifth examples may be offset from the first structure of the first layer so that the first plurality of struts of the first structure are offset from a third plurality of struts of the second structure oriented in the same direction as the first plurality of struts, the third plurality of struts being the closest parallel struts in the second layer to the first plurality of struts in the first layer. In a seventh example, the first strut of the first plurality of struts of any one of the first through sixth examples may form an X-shape with each strut in the second plurality of struts at each crossing along the first layer. In an eighth example, the second direction of any one of the first through seventh examples may be perpendicular to the first direction.

In a ninth example of the further first example, a fourth strut of any one of the first through eighth examples may be parallel and adjacent to the first strut and may include the second material at a third crossing with the second strut of the second plurality of struts and the fourth strut may further include the first material at a fourth crossing with the third strut of the second plurality of struts. In a tenth example, the first, second, third and fourth struts of the ninth example may define a substantially rectangular space between the first, second, third and fourth crossings. In an eleventh example, the rectangular spaces defined by the structure of each layer of the tenth example may form continuous channels throughout the implant. In a twelfth example, the layers of the implant of the eleventh example may define a plurality of through-holes extending from a first outer surface of the implant to a second outer surface of the implant opposite the first outer surface. In a thirteenth example, the spinal interbody implant of any one of the first through twelfth examples may further include at least a third layer adjacent and attached to the second layer, a third structure of the third layer having the first pattern throughout its surface area. In a fourteenth example, the third structure of the third layer of the thirteenth example may be offset from the second structure of the second layer and aligned with the first structure of the first layer, such that the structure of the first layer is aligned with a structure of the third layer. In a fifteenth example, a layer of any one of the first through fourteenth examples may include a pattern having a third plurality of struts oriented in a third direction between the first and second directions, the third plurality of struts intersecting with the first and second plurality of struts at the first crossing so as to define a triangular bore. In a sixteenth example, the first plurality of struts of any one of the first through fifteenth examples may have a first pattern and the second plurality of struts may have a second pattern different from the first pattern.

In a first example, a spinal interbody implant may include a peripheral wall portion having an interior surface defining an interior region. The implant may have a plurality of interconnected struts disposed within the interior region and attached to the peripheral wall portion. Each of the plurality of interconnected struts may include a matrix of a first material and a distribution of particles of a second material interspersed in the matrix. The first material may be different from the second material. In a second example, the second material of the first example may be a metal. In a third example, the first material of the first or second examples may be a polymer. In a fourth example, the first material of any one of the first through third examples may be polyether ether ketone (PEEK). In a fifth example, the particles of any one of the first through fourth may be disposed along the surface of the structure. In a sixth example, the plurality of struts of any one of the first through fifth examples may be either tubular or cuboid in shape. In a seventh example, the plurality of struts of any one of the first through eighth examples may be cuboid in shape and arranged in stacked layers, each layer including a subset of the plurality of struts.

In an eighth example, the plurality of struts of any one of the first through seventh examples may include a first layer and a second layer immediately adjacent to the first layer, the struts in the first layer being arranged in parallel and the struts in the second layer being arranged in parallel such that the struts in the second layer are oriented transverse relative to the struts in the first layer. In a ninth example, one or more of the plurality of struts of any one of the first through eighth examples may have an arched shape. In a tenth example, one or more of the plurality of struts of any one of the first through ninth examples may extend in a first direction and a second direction different from the first direction, the strut defining an acute, right or obtuse angle between the first and second directions. In an eleventh example, the plurality of struts of any one of the first through tenth examples may have a porosity between 100 and 1000 micrometers. In a twelfth example, the pore sizes of the eleventh example may vary in size and shape throughout the interior region. In a thirteenth example, each strut of the plurality of struts of the twelfth example may extend in a direction different from each of the other struts and intersect with other struts at acute angles. In a fourteenth example, each strut of the plurality of struts of any one of the first through thirteenth examples may have a unique length and size.

In a first example, a method of manufacturing an intervertebral implant may include forming a first layer of the intervertebral implant using an additive manufacturing technique and forming a plurality of additional layers using the additive manufacturing technique. Each layer may be formed in sequence and over a previous layer, until the intervertebral implant is completely formed. The intervertebral implant may include a first part with a first porosity and a second part with a second porosity different from the first porosity. The first part may include a peripheral frame of the intervertebral implant and the second part may include a plurality of discrete members disposed within the first part. In a second example, the complete forming of the intervertebral implant of the first example may occur through a single continuous process. In a third example, the forming of at least one layer from among the first layer and the plurality of layers of the first or second examples may include forming a portion of the first part and a portion of the second part. In a fourth example, the plurality of discrete members of any one of the first through third examples may be a plurality of struts that define a lattice structure. In a fifth example, the plurality of discrete members of any one of the first through fourth examples may be defined by fill disposed throughout channel openings within a body of the first part.

DETAILED DESCRIPTION

Figure 1A:
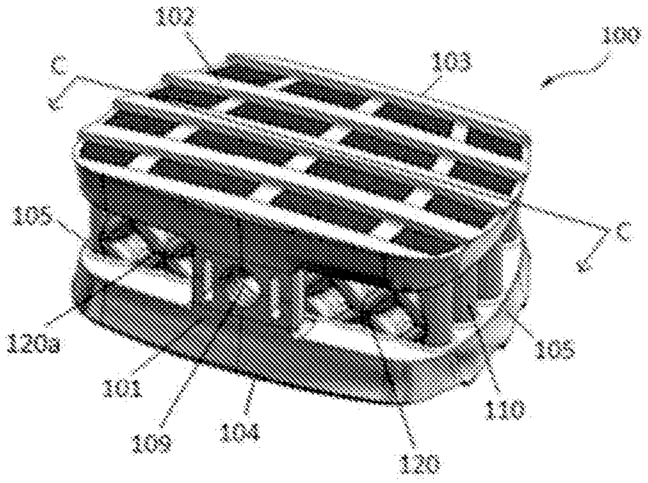
FIG. 1A is a perspective view of a spinal implant according to one embodiment of the disclosure.

Reference will now be made to the embodiments of the present disclosure illustrated in the accompanying drawings. Wherever possible, the same or like reference numbers will be used throughout the drawings to refer to the same or like features. It should be noted that the drawings are in simplified form and are not drawn to precise scale. Additionally, the term "a," as used in the specification, means "at least one." The terminology includes the words above specifically mentioned, derivatives thereof, and words of similar import.

In describing preferred embodiments of the disclosure, reference will be made to directional nomenclature used in describing the human body. It is noted that this nomenclature is used only for convenience and that it is not intended to be limiting with respect to the scope of the disclosure. For example, as used herein, when referring to the parts or ends of an implant, the term "anterior" means the end of an implant located toward the front of the body when implanted and the term "posterior" means toward the back of the body. The term "medial" means toward the midline of the implant and the term "lateral" means toward the side or sides of the body. Additionally, in the drawings and in the description that follows, terms such as front, rear, upper, lower, top, bottom and similar directional terms are used simply for convenience of description and are not intended to limit the disclosure.

It should be appreciated that although specific examples provided throughout the disclosure reference spinal implants, associated surgery and methods of spinal access, the principles set forth herein are contemplated for application in other surgical approaches or in other areas of the body where similar access is required and/or where implants with a similar structure may be utilized.

In one aspect, the present disclosure relates to an intervertebral spinal implant. The implant may be manufactured having one or a combination of the structures discussed below in further detail. In some embodiments, the implant, including both solid and porous portions, is additively manufactured, as discussed further below. In some applications of additive manufacturing, an implant that includes both solid and porous portions may be manufactured through a single continuous process. In some embodiments, the implant includes a solid material and a porous material. Use of the term "solid" in the present disclosure to describe the solid material refers to its much lower porosity, by orders of magnitude, relative to the porous material. It should be appreciated that the terms "solid" and "porous" in the context of the materials described are used to distinguish the porosity of each, and it is contemplated that implants with such solid and porous parts may still be made of the same material, such as a titanium alloy. In some examples of these embodiments, the solid portion may be constructed from titanium, titanium alloy, cobalt chromium alloy, ceramics or a polyetherketone, while the porous portion may be constructed from titanium alloy, steel, cobalt chrome and/or aluminum alloy. As a specific example, the solid material described in the embodiments herein may be titanium, such as CASCADIA® by Stryker. In another specific example, the porous material described in the embodiments herein may be a porous titanium alloy, such as TRITANIUM® by Stryker. The pores of the porous material may have an average pore diameter of 400-500 microns and an average porosity of 55-65%. In some examples, the properties of a porous material matrix within the implant are consistent throughout the matrix with a fully interconnected porosity. Such a structure is advantageous in that it has an integrated surface roughness and allows for part-specific marking. In further specific examples, an implant may have titanium as a solid material and a titanium alloy as a porous material. However, in further examples, other suitable metals or non-metals may be used, such as those listed above.

Both solid and porous materials have characteristics that can improve the performance of an intervertebral implant. For example, the solid material provides a support structure that has load bearing capacity to withstand the weight borne by the spine when in use. The solid material may be used to manufacture the outer shell of the implant, but may also include openings or through-holes to improve visibility of the implant in radiological imaging. The openings or through-holes may be any suitable shape, such as diamond, circular, square, hexagonal, or the like. The porous material provides improved visibility relative to the solid material in radiological imaging. And, the porous material further creates a favorable environment for promoting bone in-growth and proliferation to adhere and anchor the implant in a proper position between the intervertebral bodies. Further, the porous material has wicking properties so that biological fluids may be drawn into absorbed and retained by the porous structure. During this process, the wicking properties may further cause the fluid to be distributed throughout the porous structure. When used in spinal interbody applications, the porous material may allow the structure to retain the biological fluids that result from endplate preparation. And, wicking characteristics of the spinal implant may allow for retention of this nutrient-rich fluid within the porous material matrix. Such characteristics may further accelerate recovery times and improve outcomes relative to implants lacking such properties through the distribution of nutrients against gravity and through the migration and attachment of cells to the implant. Accordingly, additional advantages may be realized when the solid material and the porous material are used together in a single implant.

Figure 1B:
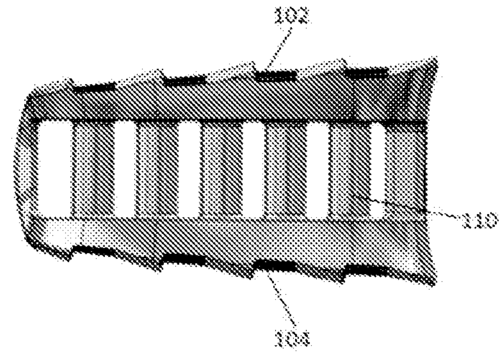
FIG. 1B is a side view of the implant of FIG. 1A
Figure 1C:
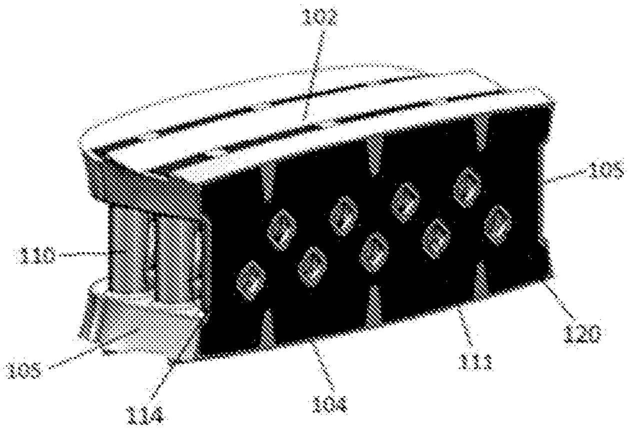
FIG. 1C is a perspective view of a cross-section of the implant of FIG. 1A taken along line C-C.

FIGS. 1A-F illustrate an implant 100 that may be used in an intradiscal space according to one embodiment of the disclosure. FIG. 1A illustrates a spinal interbody implant 100 comprising: a body comprising: a peripheral layer at least partially enclosing an inner part of the body; and an inner region within the peripheral layer, the inner region defined by a plurality of interconnected/interior/crossing tubes 120, wherein at least one tube of the interconnected tubes includes an outer tubular part/outer shell 122 and an inner fill part/core fill 126 disposed within a hollow interior of the outer tubular part, the outer tubular part being a first material with a first porosity and the inner fill part being a second material with a second porosity greater than the first porosity. Implant 100 may have surfaces defined by its orientation when placed in a mammalian spine, including superior surface 102, inferior surface 104, anterior surface 101, posterior surface 103, and lateral surfaces 105. The combination of at least some of such surfaces may define the peripheral layer. Optionally, a threaded aperture 109 is disposed on anterior surface 101 and is configured to receive a threaded insertion instrument for placement of implant 100 into the spine. Implant 100 may also include peripheral tubes 110 extending along lateral surfaces 105 of the implant, as shown in FIGS. 1A-C. Peripheral tubes 110 may be vertical tubes extending between superior surface 102 and inferior surface 104 and are spaced apart from one another at generally equal spacing. In some examples, the spacing between peripheral tubes may vary. The peripheral tubes are generally at a right angle relative to the superior and inferior surfaces. Peripheral tubes 110 may include a solid material outer layer that provides structural integrity for the implant, while an interior of such peripheral tubes may be filled with porous material 114. Between tubes 110 disposed at opposing lateral surfaces 105 is an interior region of the implant that includes a plurality of interior tubes 120. Interior tubes 120 are arranged in a three dimensional lattice configuration throughout the interior region. In the depicted embodiment, and as shown in FIG. 1A, the interior tubes are densely packed within the interior region and collectively form lattice layers along parallel planes. For example, between opposite peripheral tubes in FIG. 1A is a series of crossing tubes 120 in a single plane that may define a lattice layer 120*a*. Similar lattices are disposed spaced apart from one another generally parallel to lattice layer 120*a*. A spacing of the tubes may be varied within the interior region to obtain a desired porosity based on a distance between the tubes. Further, the tubes may be arranged in other patterns and are not limited to the series of planar constructs shown, as described in greater detail below. The collective porosity provided by tubes 120 is illustrated in FIG. 1C, which shows a cross-section of implant 100. Spaces between tubes 120 are indicated by optional holes 111.

Figure 1D:
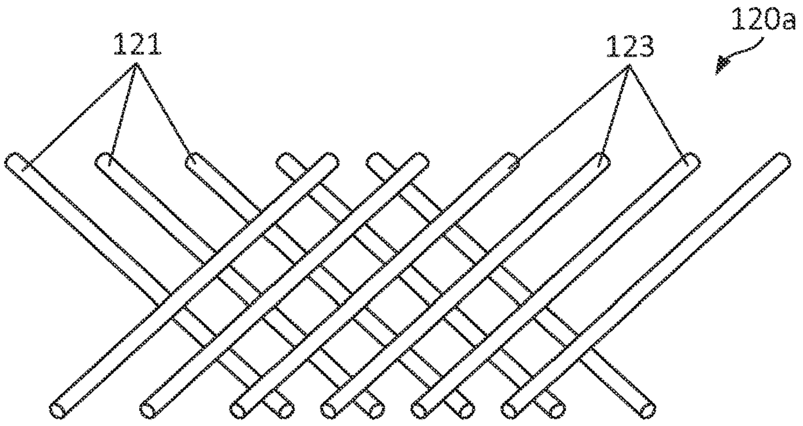
FIG. 1D is a close up view of a tube structure of the spinal implant of FIG. 1A

FIG. 1D shows tubes 120 of implant 100 in isolation. The arrangement of the tubes 120 may include a first set of tubes 121 equally spaced apart and oriented parallel to one another. The interior region may also include a second set of tubes 123 equally spaced apart and oriented parallel to one another, the orientation of the second set of tubes 123 transverse to the orientation of the first set of tubes 121. In some examples, the second set of tubes 123 are perpendicular to the first set of tubes 121 and additional sets of tubes within the interior region are arranged in a similar fashion to the first two sets. In other examples, the arrangement of the tubes 120 may be such that open spaces between the tubes are approximately equal size throughout the interior region. Although a lattice layer is shown as two sets of tubes in FIG. 1D, tubes within the interior region of the implant may include additional layers comprised of additional tubes in the same or another pattern, and in parallel or other orientations In some examples, as in the lattice layer shown, each lattice layer of tubes may extend along a plane parallel to anterior surface 101 and posterior surface 103 and perpendicular to superior surface 102 and inferior surface 104. Each lattice layer may include sets of tubes that are adjacent and aligned with the corresponding sets of tubes in adjacent lattice layers. In other examples, the sets of tubes in each lattice layer may be offset from the sets of tubes in adjacent lattice layers. In some examples, the lattice layers may extend along planes that are perpendicular or transverse to anterior surface 101 and posterior surface 103. In still further examples, the interior tubes may include a set of tubes extending between the inferior and superior surfaces and another set of tubes extending between lateral surfaces or the anterior and posterior surfaces. The first and second sets of tubes may be perpendicular to each other or may intersect to form acute and obtuse angles. The interior tubes may be perpendicular to or transverse to the outer surface of the implant. The interior tubes may have the same structure as the peripheral tubes, as described below in more detail.

Figure 1E:
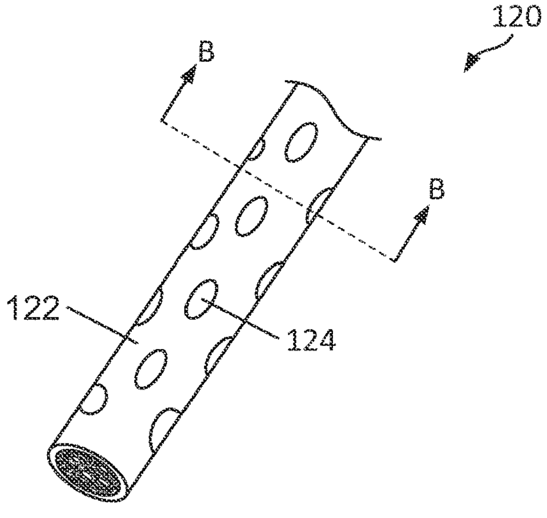
FIG. 1E is a schematic view of a single tube of the tube structure shown in FIG. 1D
Figure 1F:
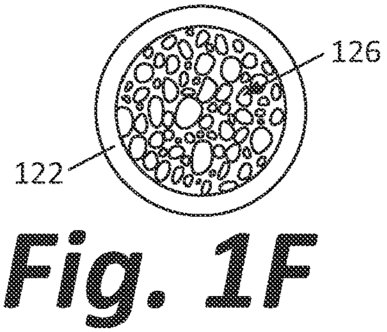
FIG. 1F is a cross-sectional view of the tube of FIG. 1E at line B-B.

Turning to the details of individual tubes within the plurality of tubes 120 occupying the interior region, FIGS. 1E and 1F provide an illustration. Each tube 120 may have an outer shell 122 of a solid material and a core fill 126 of a porous material. Outer shell 122 of tube 120 includes a series of large openings 124 along its length and around its outer perimeter, as shown in FIG. 1E. Further, FIG. 1F is a cross-sectional view of tube 120 along section B-B that shows a shape of tube 120. The porous material of core fill 114 may occupy a volume within a hollow channel of outer shell 122. As depicted, core fill 114 is not filled in large openings 124, though in variations, it may occupy such openings. In some examples, the porous material may be a foam. Constructing peripheral tubes 110 and the outer shells of tubes 122 of solid material promotes structural integrity of implant 100 for load bearing purposes. Further, by arranging interior tubes 120 in a multi-directional lattice structure within the interior of implant 100, visibility through the implant in x-rays or fluoroscopy is improved. Filling tubes 120 with core fill 114 made of porous material and including large openings 124 in outer shell 122 encourages bone ingrowth, wicking and cell attachment of implant 100 within the intervertebral space. Further, the randomized interconnected porosity of the implant structure allows cells to migrate through the heterogeneous porosity and varied pore size without pore occlusion. In other words, the structure of the interior region of the implant includes pores of varying size such that cells may freely move without blockages in the pores. Once attached to the porous structure, cells may respond to various signals, such as a roughened surface or mechanical loading on the implant, by producing and secreting protein which, over time, may mature into bone.

The implant shown in FIGS. 1A-F may be varied in many ways. For instance, it is further contemplated that the implant 100 may have a superior surface 102 parallel or non-parallel to an inferior surface 104. Another embodiment of implant 100 may include tubes 120 of different sizes, e.g., the first set of tubes 121 have a first length and diameter and the second set of tubes 123 has a second length and diameter larger or smaller than the first length and diameter. Alternatively, the length and/or diameter of each tube 120 may alternate such that every other tube in the first set of tubes 121 has the same length and/or diameter which is different from the length and/or diameter of an adjacent tube in the first set of tubes 121. Another embodiment of implant 100 may include tubes 120 arranged in an orientation such that the first and second sets of tubes 121, 123 are parallel. Tubes 120 may extend between superior surface 102 and inferior surface parallel to peripheral tubes 110 or at a transverse angle. Alternatively, tubes 120 may extend between lateral surfaces 105 and/or anterior and posterior surfaces 101, 103 perpendicular to peripheral tubes 110 or in a transverse orientation. Another embodiment of implant 100 may include non-linear tubes. For example, tube 120 may define a curve or have a changing orientation along its length. In some examples, tube 120 may extend at an acute, right or obtuse angle such that tube 120 extends between adjacent surfaces, e.g., from superior surface 102 to anterior surface 101. It is further contemplated that any combination of one or more aspects described in the alternative embodiments may be incorporated into implant 100.

Figure 2A:
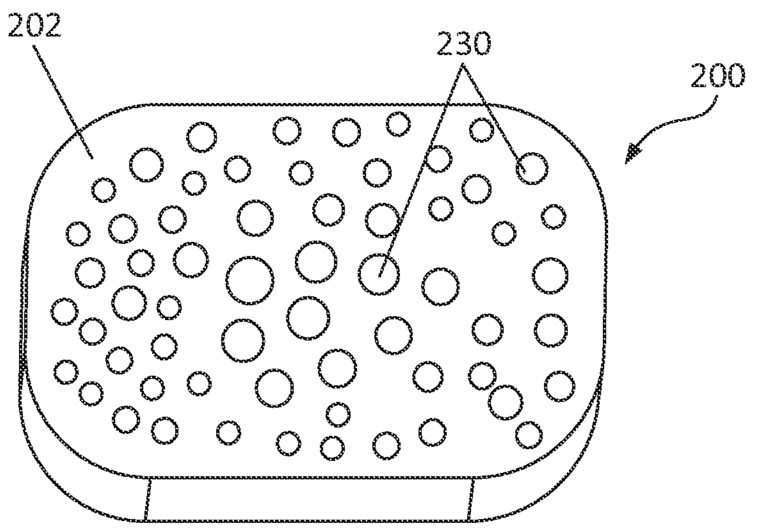
FIG. 2A is a perspective view of a superior surface of an implant according to an embodiment of the disclosure.
Figure 2B:
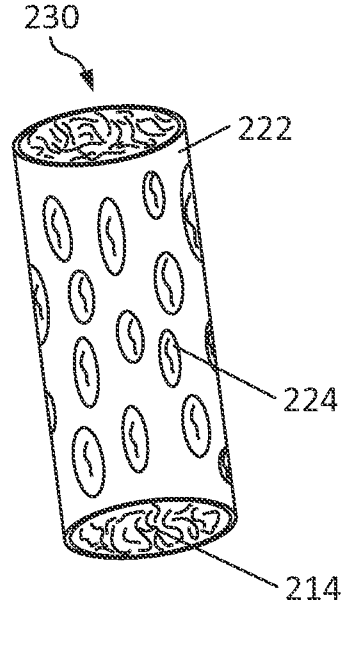
FIG. 2B is a close up view of fill within an opening of the implant in FIG. 2A.

FIGS. 2A-B illustrate an implant 200 according to another embodiment of the disclosure. FIG. 2A illustrates a spinal interbody implant 200 comprising: a body sized for placement in an intervertebral disc space, the body including a primary outer structure and a plurality of inner structures 230 disposed within channels of the primary outer structure, each of the plurality of inner structures 230 including an outer shell and an inner fill 214 with a different porosity than the outer shell, the primary outer structure having a first porosity and the inner fill of each of the plurality of inner structures 230 having a second porosity greater than the first porosity, wherein the plurality of inner structures 230 have a shape matching a shape of a respective channel, the plurality of inner structures 230 extending between opposite outer surfaces of the primary outer structure. Implant 200 includes a plurality of inner structures or shells 230 therethrough, extending from a superior surface 202 to an inferior surface (not shown) of implant 200 based on a position of implant 200 when implanted in a patient. Each shell 230 is defined by a wall 222 with pores 224 and filled with porous material 214, as shown in FIG. 2B. Shells 230 extend through implant 200 from superior surface 202 to the inferior surface. Shells 230 are cylindrical in shape and of a similar size throughout implant 200. In the illustrated embodiment, implant 200 includes shells 230 disposed in implant 200. As shown in FIG. 2B, each shell 230 has a wall 222 defining pores 224 thereon and is filled with a porous material 214. As shown, each shell 230 is a separate element that may be added into or is otherwise a separate part of implant 200 body. However, it is also contemplated that in some embodiments, an implant may have a body with channels defined therein, and the channels may be filled with a porous material. As shown, a distribution of shells 230 is generally even across implant 200, though in variations, spacing, patterns and sizes of the shells may vary. In some examples, a single implant may have shells of various sizes. In some examples, the shells have other shapes, such as diamond shapes. In other examples, the shells may extend between superior surface 202 and the inferior surface at an angle relative to a lateral surface of the implant. One or more shells may extend in any direction between any surfaces of implant 200. For instance, the shells may extend between lateral surfaces of the implant. The shells may be only partially filled with porous material, or some shells may be filled with porous material while other shells are hollow. Some shells may have fewer pores than others, and some shells may have continuous inner walls without pores. Pores on the shell wall may also vary in size and shape.

Figure 3A:
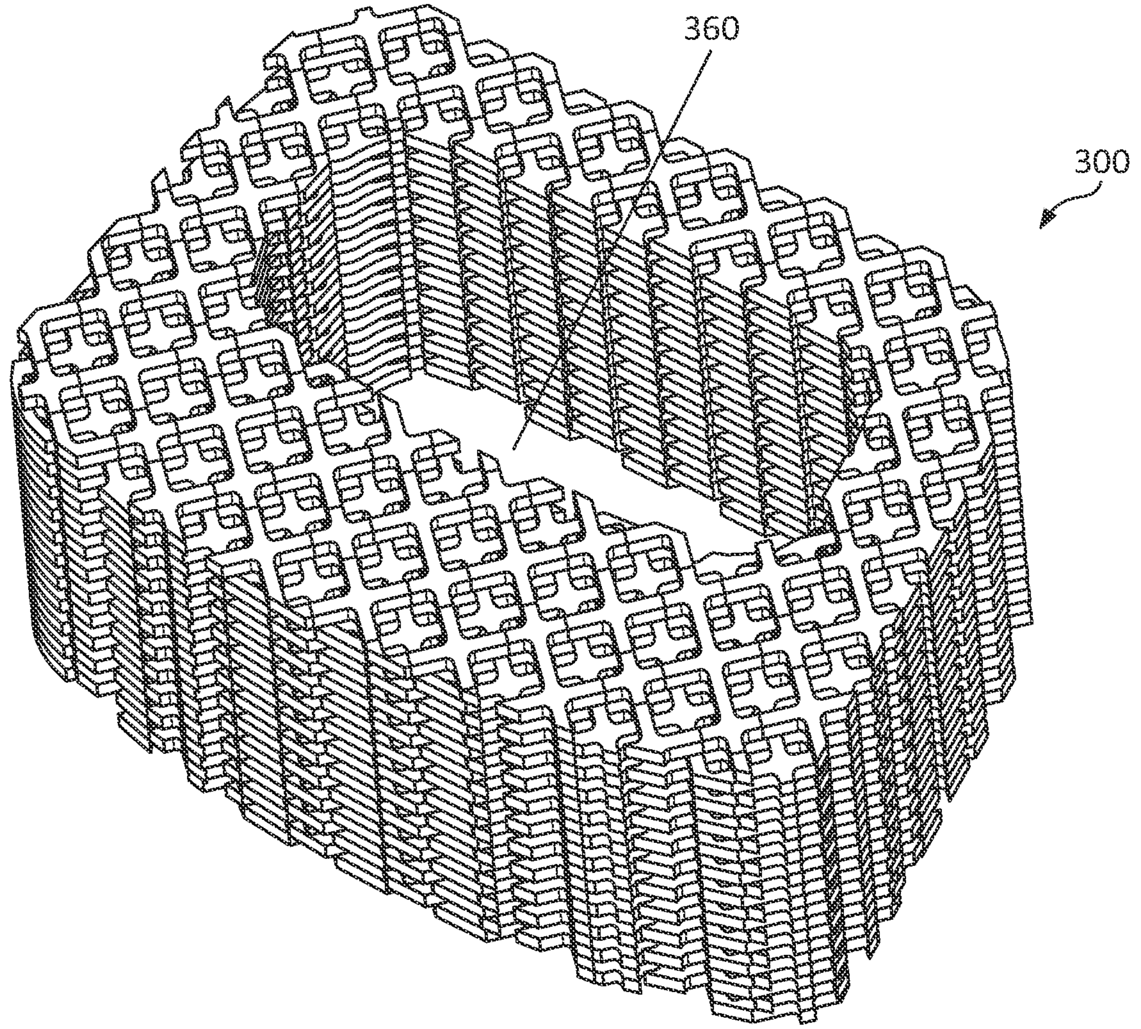
FIG. 3A is a schematic perspective view of an implant according to an embodiment of the disclosure.
Figure 3B:
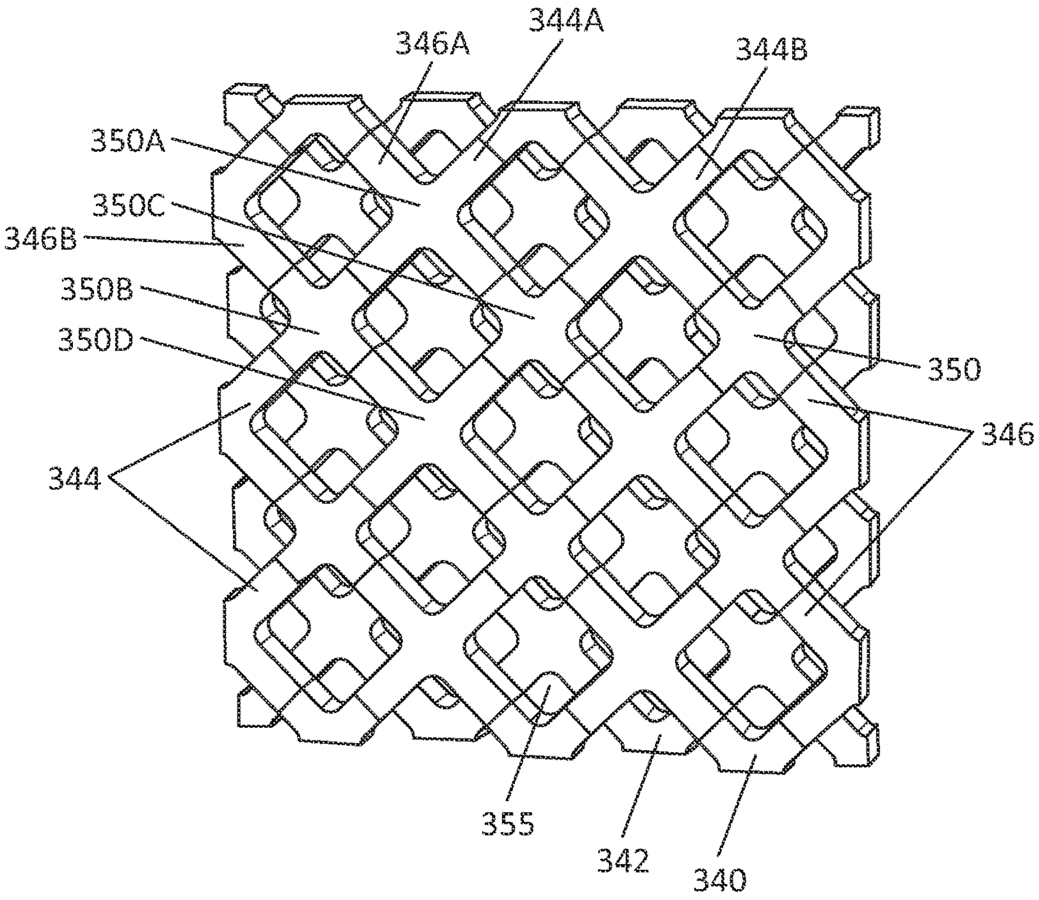
FIGS. 3B-3C are schematic views of different portions of the implant shown in FIG. 3A.
Figure 3C:
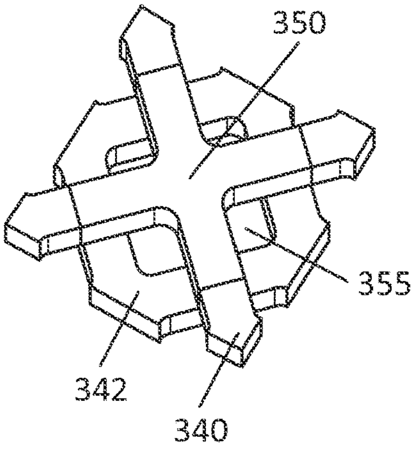
Figure 4A:
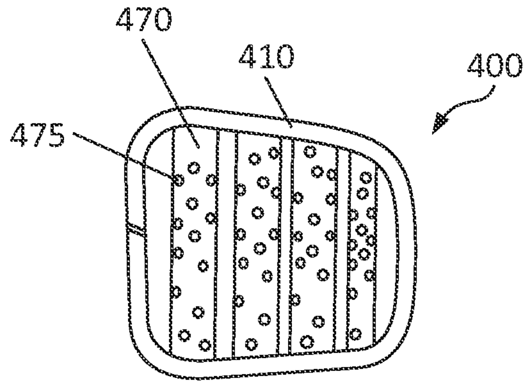
FIG. 4A is a side view of an implant according to an embodiment of the disclosure.
Figure 4B:
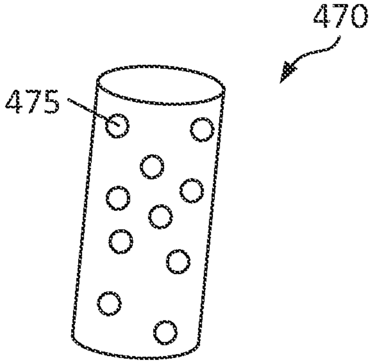
FIG. 4B is a close up view of a tubular strut of the implant of FIG. 4A.

FIGS. 3A-C illustrate an implant 300 according to yet another embodiment of the disclosure. FIG. 3A illustrates an a spinal interbody implant 300 comprising: a plurality of layers, each layer being a patterned lattice structure and interconnected with at least one other layer of the plurality of layers, the plurality of layers each comprising: a first layer 340 having a structure including a first plurality of struts 344 oriented in a first direction and a second plurality 346 of struts oriented in a second direction, at least one strut 344A of the first plurality of struts 344 crossing at least one strut 346A of the second plurality of struts 346 such that the struts are interconnected, wherein a first strut 344A of the first plurality of struts 344 has a length and has a first porosity at a first crossing 350A with a second strut 346A of the second plurality of struts 346 and a second porosity at a second crossing 350B with a third strut 346B of the second plurality of struts 346, the second strut 346A being adjacent to the third strut 346B, and wherein the first porosity is different from the second porosity. Implant 300 is a multilayered lattice structure that includes a plurality of structural layers. As shown in FIG. 3B, each layer includes alternating regions of solid material and porous material. The first layer 340, as shown in FIGS. 3B-C, comprises a first set of struts 344 in a first orientation, the struts in the first set of struts 344 arranged in parallel. The first layer 340 further includes a second set of struts 346 in a second orientation. The struts in the second set of struts 346 are arranged in parallel, and the second orientation is orthogonal to the first orientation, thereby defining a lattice structure. Each strut in both the first and second sets of struts 344, 346 includes alternating materials along its length. In particular, material that alternates between a solid material and a porous material. The material alternates such that the strut is made of a different material at each crossing 350 with a strut in the other orientation. Thus, for example, where a first strut 344A in the first set of struts 344 crosses a first strut 346A in the second set of struts, it is solid material, and where strut 344A crosses a second strut 346B in the second set, it is porous material, as shown. A plurality of struts in the first set of struts 344 orthogonally intersects with a plurality of struts in the second set of struts 346, forming a plurality of crossings 350. Each strut in the first set of struts 344 is composed of the same material as each strut in the second set of struts 346 at each crossing 350, resulting in the formation of an X-shape at each crossing 350 made of a single material. Wherein a pair of adjacent struts in the first set of struts 344 intersects a pair of adjacent struts in the second set of struts 346, four crossings 350A, 350B, 350C, 350D are formed. In particular, a first strut 344A in the first set of struts 344 intersects with a third strut 346A in the second set of struts 346 to form crossing 350A. First strut 344A intersects with a fourth strut 346B in the second set of struts 346 to from crossing 350B. An optional second strut 344B in the first set of struts 344 intersects with third strut 344A to form crossing 350C. Second strut 344B intersects with fourth strut 346B to form crossing 350D. Each crossing 350A-D may comprise a first material and be adjacent a crossing of a second material, such that two crossings positioned opposite each other in a set of four crossings 350A-D comprise the same material. Thus, crossing 350A and crossing 350D are opposite each other and both comprise the first material. Similarly, crossing 350B and crossing 350C are opposite each other and comprise the second material. Four crossings 350A, 350B, 350C, 350D define an optional rectangular bore between them. The formation of the first and second sets of struts 344, 346 creates a first layer 340 disposed within a plane. The pattern of materials for the struts is such that an overall structure of the lattice has "linear strips" of alternating materials, as shown in FIGS. 3A-B.

In the depicted embodiment, each layer includes a structure as described above, although adjacent layers are offset from one another as shown by layers 340, 342 in FIG. 3B. Cumulatively, each respective layer is stacked over and offset from an adjacent layer to form the implant 300 shown in FIG. 3A. In particular, each layer has the same structure as first layer 340. The second layer 342 is planar and adjacent and parallel to the first plane. The second layer 342 is disposed adjacent to the first layer 340, but slightly offset from the first layer 340 such that each crossing 350 in the first layer 340 is adjacent a rectangular bore 355 of the second layer 342, and vice versa. A third layer is then disposed on a third plane adjacent and parallel to the second plane, the third layer aligned with first layer 340 such that it is offset relative to second layer 342. In this manner, the third layer and second layer 342 have the same positioning relative to each other as the second layer 342 and the first layer 340. With this arrangement, each crossing 350 of the third layer aligns with a crossing 350 of the same material on the first layer 350, and each rectangular bore 355 of the third layer aligns with a rectangular bore 355 of the first layer 340. This pattern continues for each additional layer to form the implant 300 of FIG. 3A. As illustrated in FIGS. 3B-C, a crossing 350 of the first layer 340 does not completely cover the adjacent rectangular bore 355 of the second layer 342. Thus, when a plurality of layers is assembled, the rectangular bores 355 define a channel that extends between outer surfaces of implant 300. The layers of implant 300 may be assembled through additive manufacturing techniques, e.g., 3D printing, as discussed elsewhere in the disclosure. The stacked lattice structure of implant 300 improves the rotational strength of implant 300 about at least one axis. Implant 300 of FIG. 3A further includes a stadium-shaped interior cutout 360 through all layers.

The implant of FIG. 3A may be varied in many ways. The layers may have a variety of thicknesses and may vary in thickness in a particular implant. Similarly, the implant may have any number of layers suitable for manufacturing an implant sized appropriately for fitting into an intervertebral space. It is also contemplated that the implant 300 may include struts that are not arranged in parallel, or struts of various sizes such that crossings 350 vary in size and location and rectangular bores 355 do not define continuous channels between outer surfaces of implant 300. Further, each layer may not include perfectly alternating sections of the first and second materials, such that there may be sections or layers comprised of more or all of a first material and less or none of the second material, and vice versa. For example, the full first layer 340 may comprise solid titanium and the full second layer 342 may comprise porous titanium. Further, implant 300 may include a section of a layer having a group of adjacent crossings 350 comprising the same material. Some embodiments may include a layer having pattern wherein an additional set of struts is orientated at a 45 degree angle from both the first and second sets of struts forming a triangular bore between intersecting struts. In other examples, struts may be non-linear. For example, a layer may comprise a pair of struts arranged in a helical formation wherein adjacent crossings comprise different materials and define ovular bores therebetween. In another example, struts may be arranged in a plane in a random formation having no pattern such that bores defined by intersecting struts all vary in size and shape. In other embodiments, layers may define a wave pattern rather than extending in a single plane. It is also contemplated that the implant 300 may include an interior cutout 360 of a different shape or size than that which appears in FIG. 3A, or no cutout at all.

FIGS. 4-7 illustrate yet another embodiment of an implant according to the present disclosure. Implant 400, shown in FIGS. 4A-4B, includes a plurality of struts that each include a polymer matrix with metallic particles 475 distributed throughout the matrix. Implant 400 also includes a peripheral wall 410 extending around the perimeter of implant 400, as shown in FIG. 4A. Wall 100 may comprise a solid material that provides structural integrity for the implant 400. Within wall 410 is an interior region that includes a plurality of struts. In FIG. 4B, one of the struts is shown in isolation. Strut 470 may be a polymer with the metallic particles 475 interspersed throughout its volume. Metallic particles 475 may also be interspersed around the interior surface of the tubular matrix 470. In some examples, the matrices are created with a porosity between 100-1000 micrometers.

Figure 5:
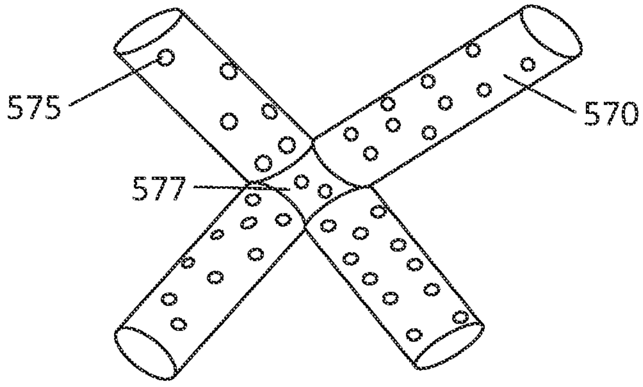
FIG. 5 is a schematic view of a strut arrangement according to an embodiment of the disclosure.

FIG. 5 illustrates struts 570 for use in the interior of an implant according to another embodiment of the disclosure. Like 500 series reference numerals refer to like elements in the 400 series of numerals. Strut 570 may be a polymer matrix with metallic particles 575 interspersed throughout. Struts 570 are arranged so that they are intersecting throughout a volume. Crossing nodes 577 between struts may represent one manner in which the struts intersect. In some examples, the struts may collectively form sheets or lattices with individual struts crossing as shown in FIG. 5, the collective struts filling a volume of a peripheral wall of an implant, such as the peripheral wall shown in FIG. 4A. In some examples, strut 570 may extend from a first surface in the interior region of implant 400 to a second surface opposing the first surface. Strut 570 may include a plurality of like struts disposed parallel to strut 570 within the interior region such that nodes 577 of the plurality of struts 570 are aligned along an axis. Alternatively, strut 570 may be coupled to additional struts 570 in the same plane forming a lattice structure.

Figure 6A:
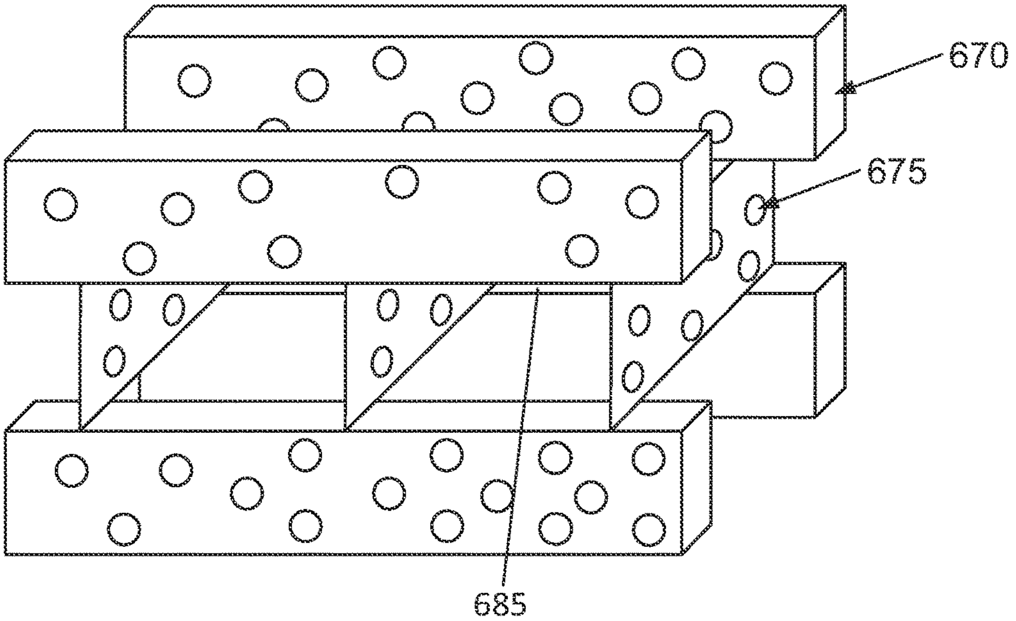
FIG. 6A is a schematic view of a strut arrangement according to an embodiment of the disclosure.
Figure 6B:
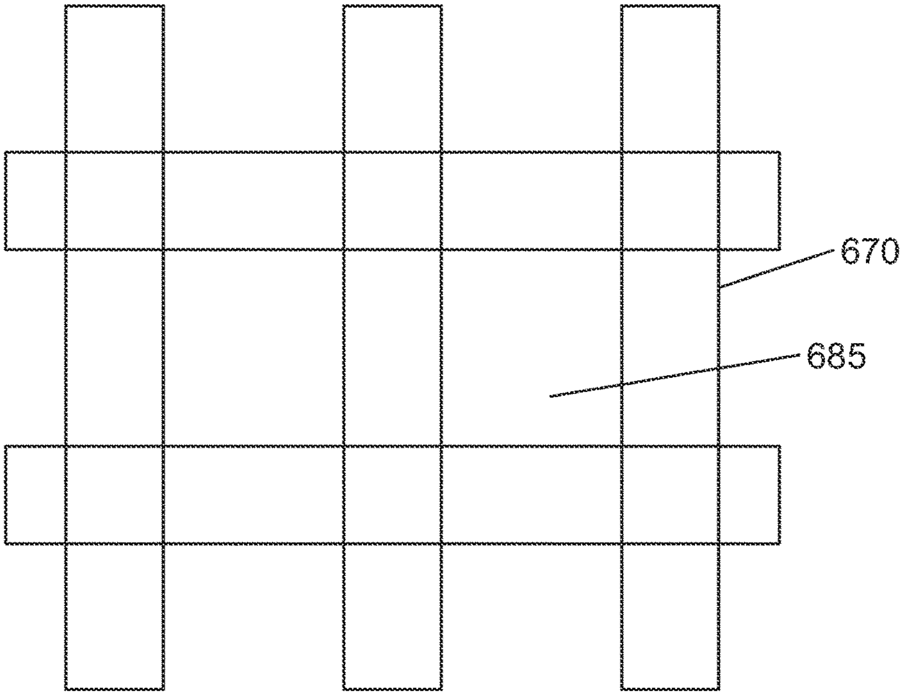
FIG. 6B is a top view of the strut arrangement shown in FIG. 6A.

FIG. 6A-6B illustrates struts 670 for use in the interior of an implant according to another embodiment of the disclosure. Like 600 series reference numerals refer to like elements in the 400 series of numerals. The struts 670 shown in FIG. 6A are a plurality of cuboid matrix elements and are arranged in multiple layers. A first layer of struts 670 may include a plurality of struts 670 oriented in parallel in a first direction. A second layer of struts 670 may include a plurality of struts 670 oriented in parallel in a second direction, wherein the second direction is perpendicular to the first direction. Struts 670 in a single layer may include a gap between adjacent struts 670 within the same layer, the gap defining a pore 685. Struts 680 may comprise a polymer matrix and include metallic particles 675 interspersed throughout.

Figure 7:
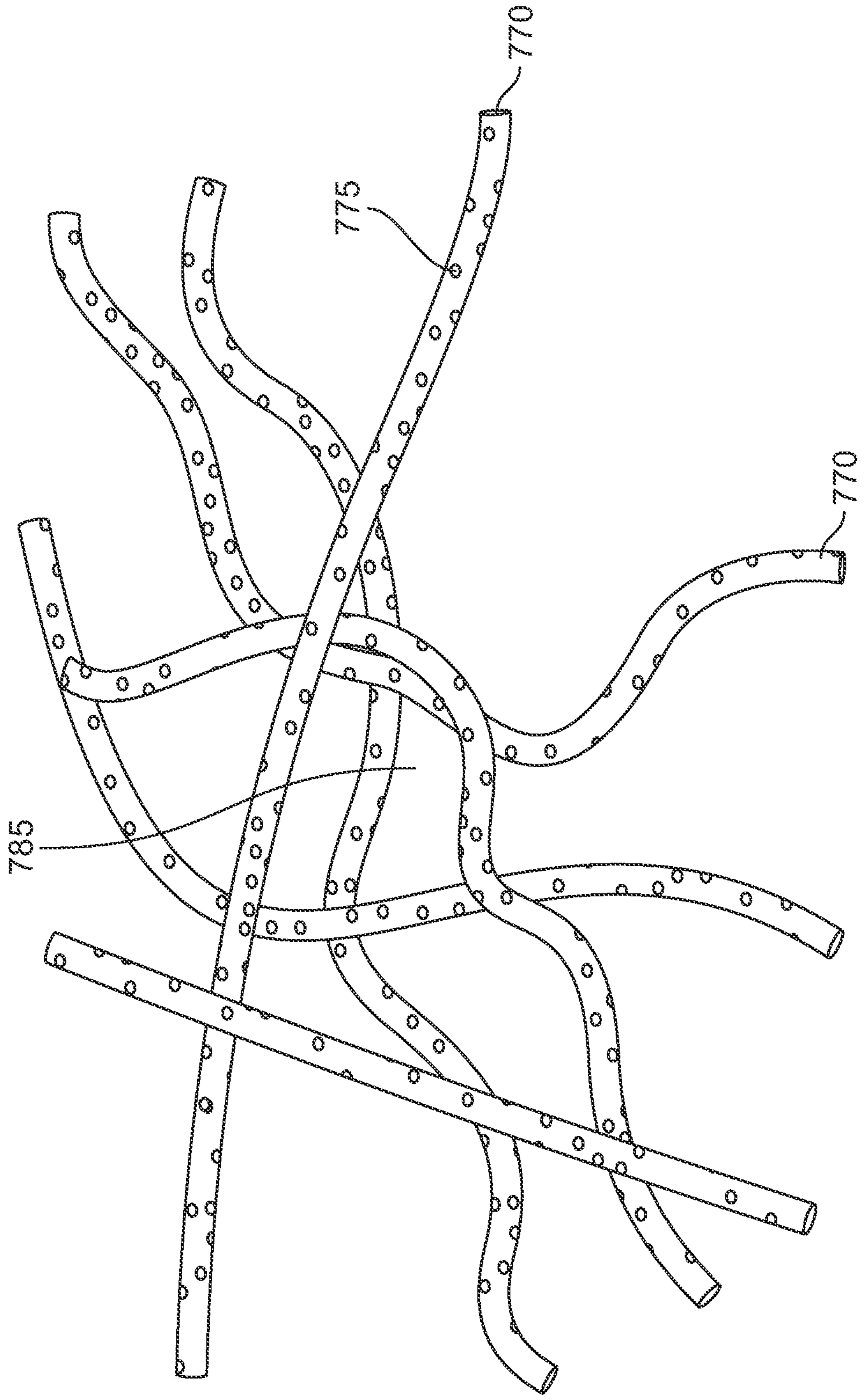
FIG. 7 is a schematic view of a strut arrangement according to an embodiment of the disclosure.

The arrangement of struts 670 may be varied in many ways. The spacing between struts may change between each pair of struts to vary size of pores, i.e., openings between each strut. Further, struts need not be straight nor arranged in parallel, but may be transverse to other struts and/or arched to form pores of varying shapes and sizes. For example, FIG. 7 illustrates yet another embodiment of struts that may be manufactured within the interior surface of implant 400. Like 700 series reference numerals refer to like elements in the 400 series of numerals. FIG. 7 illustrates a plurality struts 770 shaped and arranged to be overlapping in a scattered arrangement to create a range of pore 785 sizes. Struts 770 are polymer matrices of various shapes and sizes having metallic particles 775 interspersed throughout. In the embodiment as depicted, each strut 770 is a different size and shape than the other struts in the plurality of struts 770. Further, each strut 770 extends in a direction transverse to other struts 770 and struts 770 intersect at different angles.

Specific materials for the polymer matrix and the metallic particles may vary. In some examples, struts 470, 570, 670, 770 may be composed of a matrix made of a ceramic material polyether ether ketone (PEEK). In some examples, metallic particles 475, 575, 675, 775 may comprise Bioglass or any other bioresorbable material.

In another aspect, the present disclosure relates to a method of manufacture of an implant including the various implants described in the present disclosure. In some embodiments, the implant may be formed using a layered additive manufacturing or a 3D printing process, e.g., using Laser Rapid Manufacturing (LRM) technology, electron beam melting (EBM), selective laser sintering (SLS), selective laser melting (SLM), and/or blown powder fusion for use with metal powders. When employing these technologies, articles are produced in layer-wise fashion from a laser-fusible powder that is dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. Detailed descriptions of the SLS technology may be found in U.S. Pat. Nos. 4,863,538, 5,017,753, 5,076,869, and 4,944,817, the entire disclosures of which are incorporated by reference herein. Similarly, a detailed description of the use of SLM technology may be found in U.S. Pat. No. 7,537,664, the disclosure of which is incorporated by reference herein.

The SLM and SLS technologies have enabled the direct manufacture of solid or porous three-dimensional articles of high resolution and dimensional accuracy from a variety of materials including wax, metal and metal alloys, metal powders with binders, polycarbonate, nylon, other plastics and composite materials, such as polymer-coated metals and ceramics. Techniques such as but not limited to SLS, three-dimensional inkjet printing (3DP), stereolithography (SLA), fused filament fabrication (FFF) and fused deposition modeling (FDM®) may be used with polymer powders or strands to produce polymeric constructs. FDM® or FFF may be used with various polymers (e.g., thermoplastics, elastomers) and waxes. Cellular scaffolds may be formed using bioplotters or 3DP. The aforementioned technologies may be used to manufacture unitary constructs that include multiple material types. For instance, implants that include a solid outer shell and a porous interior may be manufactured utilizing the described additive manufacturing technologies.

In an example of constructing a tangible structure from a model build geometry using metal powder, a layer of metal powder may be deposited onto a substrate. The substrate may be a work platform, a solid base, or a core, with the base or core being provided to possibly be an integral part of the finished product. In inkjet 3D printing, a liquid binding material is selectively deposited across a thin layer of a powder and the process is repeated in which each new layer is adhered to the previous layer. In some embodiments, individual layers of metal may be scanned using a directed high energy beam, such as a continuous or pulsed laser or e-beam system to selectively melt the powder, i.e., melt the powder in predetermined locations. Each layer, or portion of a layer, is scanned to create a plurality of predetermined porous or mesh physical constructs, and when necessary predetermined solid constructs, by point exposure to the energized beam. This leads to the production of linear, curvilinear, or other shaped struts that correspond to the segments described previously herein and ultimately to a final construct. Successive layers are deposited onto previous layers and also are scanned. The scanning and depositing of successive layers continues the building process of the predetermined solid and/or porous geometries. As disclosed herein, continuing the building process refers not only to addition of a layer of a physical construct to a previous layer but also a beginning of a new physical construct as well as the completion of the current physical construct.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A spinal interbody implant comprising:

a peripheral layer including a plurality of struts extending vertically between an upper plate and a lower plate, the plurality of struts defining a first row of struts and a second row of struts, wherein the first and second row of struts are positioned at opposite sides of the peripheral layer; and an inner region within the peripheral layer, the inner region defined by a plurality of interconnected tubes, wherein the plurality of interconnected tubes define lattice layers oriented substantially in parallel planes spaced apart from each other, each of the lattice layers is formed of interconnected tubes crossing in a single plane, the lattice layers extend from the first row of struts to the second row of struts, wherein two or more of the interconnected tubes have a first end on a surface of the upper plate and a second end on a surface of the lower plate such that the upper and lower plates cover the inner region and extend from the first row of struts to the second row of struts, and wherein at least one tube of the plurality of interconnected tubes includes an outer tubular part and an inner fill part disposed within a hollow interior of the outer tubular part, the outer tubular part being a first material with a first porosity and the inner fill part being a second material with a second porosity greater than the first porosity.

2. The spinal interbody implant of claim 1, wherein:

the first material and the second material are the same.

3. The spinal interbody implant of claim 1, wherein:

the first material is titanium and the second material is a titanium alloy.

4. The spinal interbody implant of claim 1, wherein:

the plurality of interconnected tubes are disposed evenly throughout the inner region.

5. The spinal interbody implant of claim 1, wherein: each lattice layer comprises a first group of tubes and a second group of tubes, the first group of tubes being approximately in parallel with one another and oriented in a first direction, and the second group of tubes being approximately in parallel with one another and oriented in a second direction different from the first direction.

6. The spinal interbody implant of claim 1, wherein: the outer tubular part of the at least one tube of the plurality of interconnected tubes includes a series of openings therethrough.

7. The spinal interbody implant of claim 6, wherein:

the series of openings through the outer tubular part of the at least one tube are filled with the second material.

8. The spinal interbody implant of claim 1, wherein the upper plate includes slanted struts extending from a first side of the implant to a second side of the implant, the slanted struts including a first strut spaced generally equal distances from third and fourth opposing sides of the implant.

9. The spinal interbody implant of claim 1, wherein an exterior wall of the implant defines a threaded aperture configured to receive a tool.

10. The spinal interbody implant of claim 9, wherein the exterior wall is defined by a central support member extending between the upper and lower plates and spaced generally an equal distance from the first and the second rows of struts.

11. The spinal interbody implant of claim 10, wherein the central support member is integral to the upper and lower plates.

12. A spinal interbody implant comprising:

a plurality of peripheral tubes extending vertically between an upper plate and a lower plate, the plurality of peripheral tubes defining a first row of exterior tubes and a second row of exterior tubes located on opposite sides of the implant from each other; and an interior region located between the first and second rows of exterior tubes, the interior region defined by a plurality of interior tubes, wherein the plurality of interior tubes define lattice layers oriented substantially in parallel planes spaced apart from each other, each of the lattice layers is formed of interior tubes crossing in a single plane, the lattice layers extend from the first row of exterior tubes to the second row of exterior tubes, wherein the plurality of interior tubes includes two or more interconnected tubes, the two or more interconnected tubes extending transverse to the upper plate and the lower plate, and wherein at least one tube of the plurality of interior tubes includes an outer tubular part and an inner fill part disposed within a hollow interior of the outer tubular part, the outer tubular part being a first material with a first porosity and the inner fill part being a second material with a second porosity greater than the first porosity.

* * * * *